United States Patent [19]
Murase

[11] Patent Number: 5,340,312
[45] Date of Patent: Aug. 23, 1994

[54] ANTI-CONTAMINATION TYPE ELONGATED HAND PIECE OF A DENTAL INSTRUMENT

[76] Inventor: Masahiro Murase, 27-4, Nishi-Kamata 6-chome, Ohta-ku, Tokyo, Japan

[21] Appl. No.: 70,287

[22] Filed: Jun. 2, 1993

[30] Foreign Application Priority Data

Jun. 9, 1992 [JP] Japan .................. 4-173690

[51] Int. Cl.⁵ ........................... A61C 1/05
[52] U.S. Cl. ..................... 433/132; 415/904
[58] Field of Search ............. 433/132; 415/904

[56] References Cited
U.S. PATENT DOCUMENTS

| | | | |
|---|---|---|---|
| 3,076,267 | 2/1963 | Hoffmeister et al. | 433/132 |
| 3,175,293 | 3/1965 | Borden | 433/132 |

FOREIGN PATENT DOCUMENTS 3-46743 10/1991 Japan .

*Primary Examiner*—John J. Wilson
*Attorney, Agent, or Firm*—Nikaido Marmelstein Murray & Oram

[57] ABSTRACT

In order to prevent invading of blood, saliva and other impurities inside of an elongated hand piece of a dental instrument for preventing infection, the inside contamination-free elongated hand piece has rectilinear means in the airholes of upper and lower lids of its head housing, thereby assuring that air flowing out from the head housing is rectified to helical stream, thereby causing no Karman's vortex street behind. The rectilinear means may be given in the form of helical ridges or slots formed on the inner surface of each airhole.

4 Claims, 3 Drawing Sheets

ANTI-CONTAMINATION TYPE ELONGATED HAND PIECE OF A DENTAL INSTRUMENT

BACKGROUND OF THE INVENTION

1. FIELD OF THE INVENTION

The present invention relates to the elongated hand piece of a dental instrument or 3-way syringe/water and air regulator having means to prevent contamination of the inside of the elongated hand piece.

2. DESCRIPTION OF RELATED ART

A dental instrument or 3-way syringe/water and air regulator is used by putting its tool in the mouth of a patient to cut or grind selected teeth, and therefore, the end of the instrument is most likely contaminated with blood or saliva, which is liable to invade the inside of the elongated hand piece. Even if the outer surface of the instrument is sanitized, blood, saliva or other impurities remain inside, and therefore the instrument cannot be completely sanitized. If the inside-contaminated instrument is used in the mouth of another patient, such impurities may be released, and therefore, there is a fear of patients being infected with different diseases through the agency of inside-contaminated dental instruments.

There is a strong demand for preventing infection through the agency of inside-contaminated dental instruments by removing blood, saliva or other impurities from the inside of dental instruments. Japanese Utility Model 3-46743(B) discloses an inside contamination-free dental instrument whose elongated hand piece has an air turbine driven by compressed air. The air turbine is rotatably mounted in an associated head casing with the aid of upper and lower bearings, and the head casing has upper and lower lids. Annular slots and annular air cells are formed in the inside of the head casing particularly in the vicinity of the apertures of the upper and lower lids through which apertures the shaft of the air turbine extends, and an air feeding passage communicates with the annular slots and annular air cells. In use air is made to flow in the air feeding passage, allowing air to flow through the annular gaps between the shaft of the air turbine and the circumference of the aperture of each of the upper and lower lids while keeping the inside of the head casing at an increased pressure, thus preventing invasion of blood, saliva or other impurities from the exterior.

Karman's vortex street, however, is liable to appear in the air flow, particularly in the annular slot and annular cell, thereby causing a counter air flow in the annular gaps around the shaft of the air turbine in the upper and lower lids, thus introducing air inside.

As a result, blood, saliva and other impurities in a patient's mouth are liable to be air-borne to the inside of the dental instrument, and these impurities attach on the annular slots and cells. As a result bacilli will increase within the dental instrument, and then the inside of the dental instrument will be contaminated with such bacilli.

SUMMARY OF THE INVENTION

One object of the present invention is to provide a dental instrument which is capable of preventing blood, saliva and other impurities in the mouth from invading the inside of the instrument, thereby keeping the inside of the dental instrument in good sanitary condition.

To attain this object an anti-contamination type elongated hand piece of a dental instrument comprising a head housing having upper and lower lids, and a tool drive to permit the detachable mounting of a tool, said tool drive being fixed in said head housing with its drive shaft rotatably supported by upper and lower bearing means, is improved according to the present invention in that: upper and lower air cells are defined by said upper lid and said upper bearing means and by said lower lid and said lower bearing means; said upper and lower air cells communicating with air supply passages; and said upper and lower lids have airholes to permit air to flow out from said air cells, said air holes having rectilinear means for ensuring rectilinear flow so as to rectify the airflow therethrough.

According to one aspect of the present invention said rectilinear means comprises a plurality of helical or spiral ridges or grooves.

According to another aspect of the present invention said upper and lower air cells have a same capacity, and said upper and lower lids have airholes of same size to permit air to flow out at same rate.

According to still another aspect of the present invention said elongated hand piece has a chip purging air passage opening at its neck or in said lower lid, the opening part of said chip purging air passage having rectilinear means.

With this arrangement no Karman's vortex street can appear in the vicinity of the portions of the dental instrument at which air flows out from the inside of the instrument, particularly around the airholes of the upper and lower lids and the opening of the chip purging air passage, thus preventing the drawing of air from the exterior to the inside of the instrument to keep the inside of the instrument in good sanitary condition.

Other objects and advantages of the present invention will be understood from the following description of preferred embodiments of the present invention, which are shown in accompanying drawings.

DESCRIPTION OF THE PREFERRED EMBODIMENTS

Figure 1:
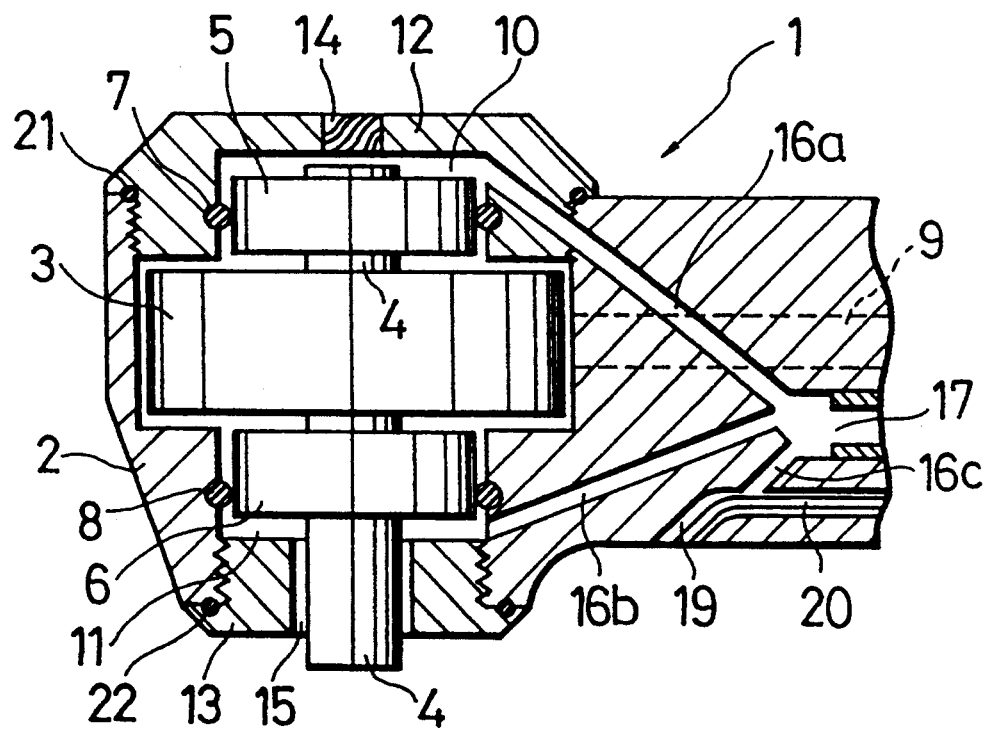
FIG.1 is a longitudinal section of the head of an anti-contamination type elongated hand piece of a dental instrument according to one embodiment of the present invention.
Figure 2:
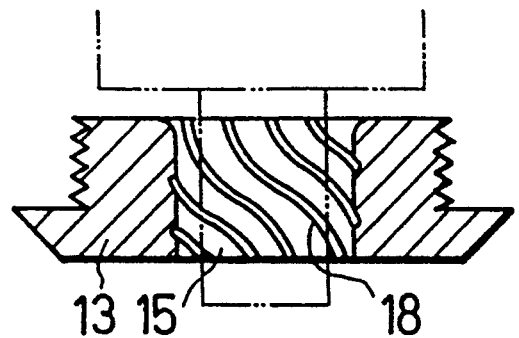
FIG.2 is an enlarged section of the lower lid of the head of the elongated hand piece of FIG. 1.

FIGS.1 and 2 show an anti-contamination type elongated hand piece of a dental instrument according to a first embodiment of the present invention. The inside contamination-free elongated hand piece 1 comprises a head housing 2 having upper and lower lids 12 and 13, and a tool drive 3 such as an air-turbine to permit the detachable mounting of a tool such as a cutter or drill bit. The air-turbine 3 has a drive shaft 4, which is rotatably borne by upper and lower bearing members 5 and 6.

These bearing members 5 and 6 are fixed to the inside of the housing 2 via "O" rings 7 and 8 hermetically. An air circulating path 9 communicates to the air-turbine 3. The air circulating path 9 is composed of a parallel arrangement of air-supplying and air-returning ducts for driving the air-turbine 3.

An upper air cell 10 is defined by the upper bearing member 5 and the upper lid 12 whereas a lower air cell 11 is defined by the lower bearing member 6 and the lower lid 13. These lids 12 and 13 have airholes 14 and 15 to permit air to flow out from the air cells 10 and 11, and air feeding paths 16a and 16b communicate to the air cells 10 and 11 respectively.

As shown, these air feeding paths 16a and 16b branch from an air storage 17, and are supplied with air under some pressure.

Rectilinear means 18 is formed on the inner circumference of the airhole 14 or 15 of each lid to rectify the airflow therethrough. The rectilinear means 18 is a plurality of helical or spiral ridges or grooves to permit the air to flow helically without causing disturbance. In the course of ejection of air fed via the air feeding paths 16a and 16b no Karman's vortex street can be caused in the air cells 10 and 11 and the airholes 14 and 15.

Preferably the air cells 10 and 11 have a same capacity, and the upper and lower lids 12 and 13 have airholes of same size to permit air to flow out at same rate. Thus, aerodynamic balancing can be assured in the upper and lower spaces of the head housing. This aerodynamic balancing and the disturbance-free air ejection assure no drawing of air from the exterior to the inside of the dental instrument, thereby preventing the inside contamination.

As seen from FIG.1, a chip purging air passage 19 and a water pipe 20 are formed in the head housing 2, opening at the neck of the elongated hand piece A rectilinear means 18 is formed on the inside circumference of the chip purging air passage 19 in the form of helical ridges or slots. The chip purging air passage 19 communicates with an air feeding passage 16c which branches from the air storage 1.

The blowing of air from the chip purging air passage 19 will draw water out of the water pipe 20 to spray water at a selected part of the mouth, which part is being subjected to dental treatment. The air blows from the chip purging air passage 19 in the regulated, helical stream. Thus, there appears no Karman's vortex street, causing no suction of impurities to the inside of the dental instrument. Therefore, there is no fear of inside contamination.

Even when no air is supplied from the chip purging air passage 19, the opening of the chip purging air passage 19 remains at an increased pressure because air flows from the air feeding path 16c, and the air flows in the helical stream, causing no Karman's vortex street behind. Thus, there is no fear of inside contamination when there is no chip purging air flowing from the opening of the chip purging air passage 19.

Figure 4:
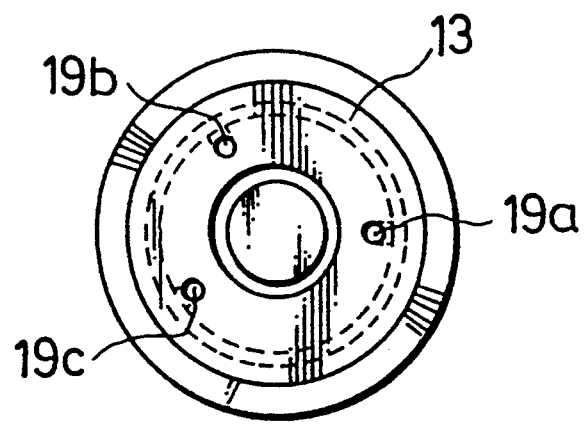
FIG.4 is a bottom view of the head of the elongated hand piece of FIG.2.
Figure 3:
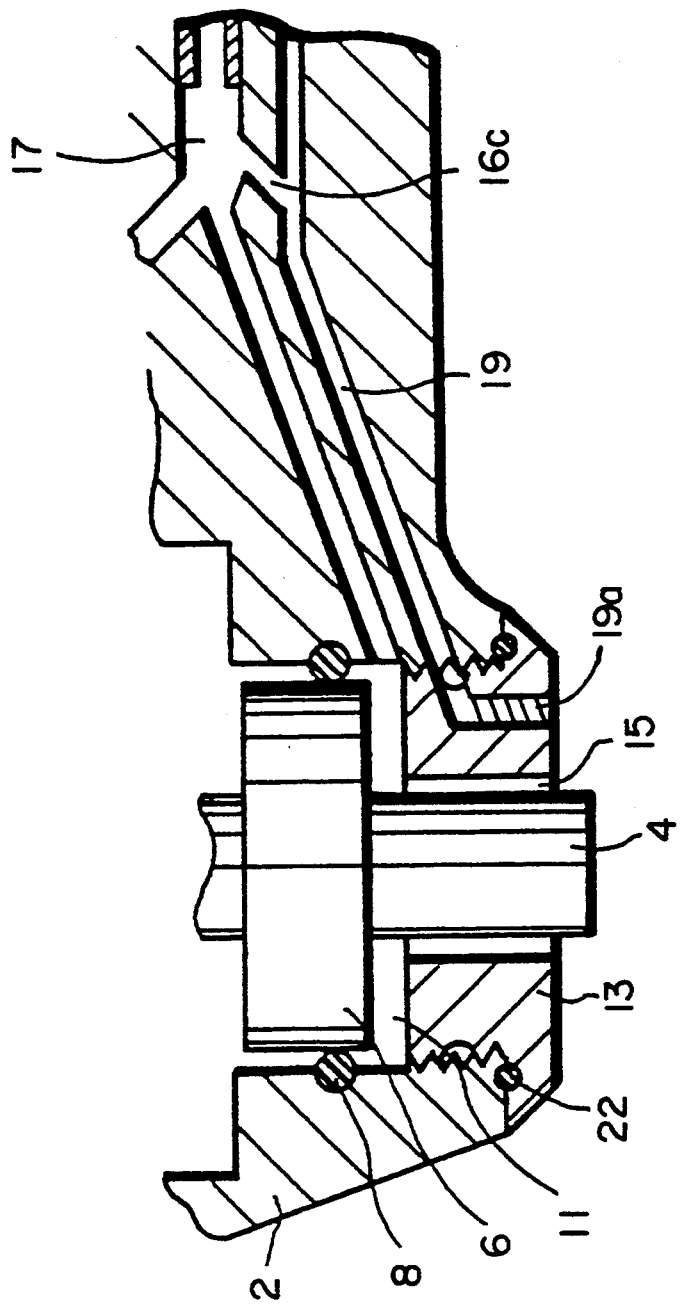
FIG.3 is a longitudinal section of a fragment of the head of an anti-contamination type elongated hand piece according to another embodiment of the present invention.

FIGS.3 and 4 show an anti-inside contamination type elongated hand piece of a dental instrument according to a second embodiment of the present invention. This inside contamination-free elongated hand piece is different from the first embodiment only in the structure of chip purging air passage 19. Specifically, the lower lid 13 has a plurality of (three) airholes 19a, 19b and 19c for the chip purging air passage 19. These airholes 19a, 19b and 19c have rectilinear means in the form of helical ridges or slots to prevent appearance of Karman's vortex street and hence inside contamination.

The inside contamination-free dental instruments are described as using an air turbine for driving an associated tool. A rotary or gear type drive can be equally used. "O" rings 21 and 22 are used to hermetically seal the upper and lower lids.

In operation the air turbine 3 rotates to cut or drill a selected tooth in the mouth with its tool while the airflows from the air feeding passages 16a and 16b keep the air cells 10 and 11 at an increased pressure, and the helical air streams flowing out from the airholes 14 and 15 of the upper and lower lids 12 and 13 leave no Karman's vortex behind in the air cells 10 and 11, thus causing no suction of impurities to the inside of the dental instrument.

Whether the chip purging air flows or not, the inner pressure remains high, and the helical stream of air flows out from the airholes of the lower lid 13 all the time, causing no Karman's vortex behind. Therefore, there is no fear of suction of impurities to cause inside contamination.

As may be understood from the above, an inside contamination-free arm of a dental instrument has rectilinear means in the airholes of upper and lower lids of its head housing, thereby assuring that air flowing out from the housing is rectified to helical stream, thereby causing no Karman's vortex behind. The rectilinear means may be given in the form of helical ridges or slots formed on the inner circumference of each airhole. Thus, there is no fear of suction of blood, saliva or other impurities to the inside of the dental instrument. Preferably the upper and lower air cells in the head housing may have a same capacity, and the upper and lower lids have airholes of same size so that aerodynamic balancing may be assured in the upper and lower areas of the head housing, thus eliminating the possibility of suction of air from outside.

I claim:

1. An anti-contamination type elongated hand piece of a dental instrument comprising: a head housing having upper and lower lids, and a tool drive to permit the detachable mounting of a tool, said tool drive being fixed in said head housing with its drive shaft rotatably supported by upper and lower bearing means, characterized in that: upper and lower air cells are defined by said upper lid and said upper bearing means and by said lower lid and said lower bearing means; said upper and lower air cells communicating with air supply passages; and said upper and lower lids have airholes to permit air to flow out from said air cells, said air holes having rectilinear means for ensuring rectilinear flow to rectify the airflow therethrough.

2. An anti-contamination type elongated hand piece of a dental instrument according to claim 1, wherein said rectilinear means comprises a plurality of helical ridges or grooves.

3. An anti-contamination type elongated hand piece of a dental instrument according to claim 1 or 2, wherein said upper and lower air cells have a same capacity, and said upper and lower lids have airholes of same size to permit air to flow out at the same rate.

4. An anti-contamination type elongated hand piece of a dental instrument according to claim 1, wherein said hand piece has a chip purging air passage opening at its neck or in said lower lid, the opening part of said chip purging air passage having rectilinear means for ensuring rectilinear flow to rectify the airflow therethrough.

* * * * *